United States Patent [19]

Elmi

[11] 4,018,225
[45] Apr. 19, 1977

[54] CATAMENIAL TAMPON

[75] Inventor: Stelio Jack Elmi, Andover, Mass.

[73] Assignee: The Gillette Company, Boston, Mass.

[22] Filed: Aug. 18, 1975

[21] Appl. No.: 605,427

[52] U.S. Cl. .............................. 128/285; 128/270
[51] Int. Cl.$^2$ ...................................... A01F 13/20
[58] Field of Search ................. 128/270, 285, 263

[56] References Cited

UNITED STATES PATENTS

| | | | |
|---|---|---|---|
| 1,743,733 | 1/1930 | Spardel | 128/285 |
| 1,884,089 | 10/1932 | Millner | 128/285 |
| 2,031,638 | 2/1936 | Emery, Jr. | 128/285 |
| 2,330,257 | 9/1943 | Bailey | 128/285 X |
| 3,085,574 | 4/1963 | Penska | 128/263 |
| 3,298,369 | 1/1967 | Pirie | 128/285 |
| 3,749,094 | 7/1973 | Duncan | 128/285 |
| 3,815,601 | 6/1974 | Schaefer | 128/285 |

Primary Examiner—Aldrich F. Medbery
Attorney, Agent, or Firm—Richard A. Wise; Oistein J. Bratlie; William M. Anderson

[57] ABSTRACT

The present invention is concerned with catamenial tampons which comprise means for preventing by-pass but yet are readily removable. Generally the tampons are hollow cones of absorbable material with a withdrawal cord attached to the apex and an unfurlable cuff around the outside of the open base end of the cone.

5 Claims, 3 Drawing Figures

CATAMENIAL TAMPON

One of the major problems in the designing of tampons is that if they are made large enough to make firm contact with the vaginal walls to prevent by-pass, they are difficult to remove when in a saturated and swollen state. The present invention is concerned with tampons which can make firm contact with the vaginal walls but yet can be readily removed in their swollen, saturated state.

One object of the present invention is to provide tampons which can make firm contact with the vaginal walls and thus reduce the possibility of by-pass.

Another object is to provide such tampons which are also readily removable when in a swollen state.

Other objects should be clear from the specification, claims, and drawings wherein:

Generally the tampons of the present invention are of the type intended to occupy about one-third of the anterior portion of the vagina just posterior of the hymenal ring. As stated above the tampons are in the form of hollow cones, and when positioned the apex will lie in the anterior portion of the vagina and the open end of the base of the cone will face the posterior portion.

Figure 1:
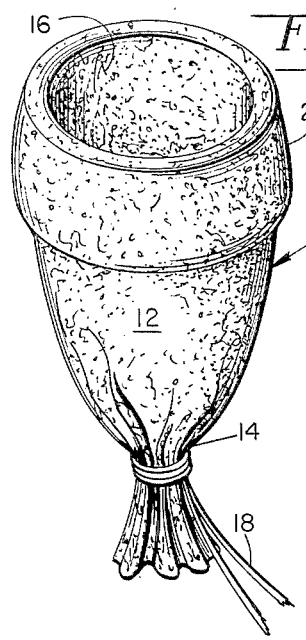
FIG. 1 is a perspective view of a preferred tampon within the scope of the present invention.
Figure 2:
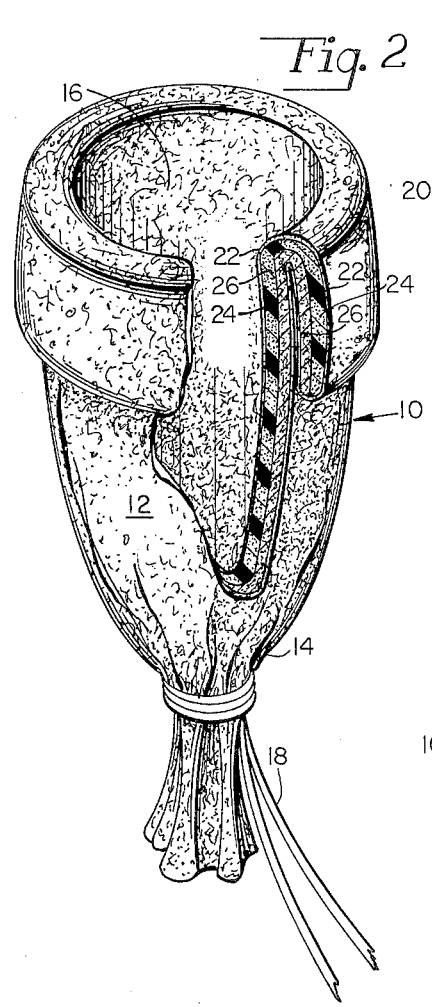
FIG. 2 is a perspective view of the tampon of FIG. 1 with portions of the cuff and side wall of the cone cut away to reveal their make-up.

With reference to FIG. 1 the tampon 10 comprises a hollow cone 12 having an apex portion 14 and an open ended base 16. Attached to the apex 14 of the cone 12 there is a cord 18 for removing the tampon 10 when it becomes saturated. At the open end 16 there is a cuff 20 which is furled partway down the outer walls of the cone 12. The cuff 20 unfurls when the tampon is removed. Generally the height and circumference of the tampon may vary. Usually with the cuff 20 furled, the height of the tampon will generally lie between about 1 ½ and 3 inches and preferably will be about 2 inches, and the outer circumference of the furled cuff generally will be between 3 and 6 inches and preferably will lie between 5 and 6 inches. Generally the tampon 10 can be constructed of the various absorbent materials which have been used in products of this nature. As an example of a preferred structure reference may be made to FIG. 2 wherein the preferred tampon 10 of FIG. 1 is shown with a portion of the cuff 20 and the side wall of the cone 12 cut away. Generally the tampon 10 comprises an outer layer 22 of non-woven absorbent, permeable fabric which surrounds the inner and outer surfaces of the cone, an absorbent fibrous layer 24, e.g., a mat or short length cellulose fibers such as wood pulp or cotton linters, and an absorbent foam layer 26 such as Hydro-Foam water-absorbable polyurethane foam sold by Scott Paper Company.

In a preferred embodiment of the present invention at least one of the fiber 24 or foam 26 layers includes or bares a highly absorbent, hydrophilic, water-insoluble polymer. As examples of such polymers mention may be made of partially hydrolyzed graft polymers of acryonitrile on starch; water-insoluble, hydrophilic, polyethylene oxides such as disclosed in U.S. Pat. Nos. 3,664,343 and 3,783,872; and slightly crosslinked, water-insoluble, highly water absorbent, polyvinyl pyrrolidines, sulfonated polystyrene, polyhydroxy ethyl acrylates and methacrylates, hydrolyzed polyacrylamides, and copolymers of acrylamide and acrylic acid.

Generally the tampons 10 may be formed by first forming a truncated cone-like structure from the (a) non-woven cloth 22, (b) the fiber mat 24, and (c) the absorbent foam 26, then gathering in the truncated end and attaching the withdrawal cord 18 and thereafter rolling down the cuff 20. Generally the distance the cuff 20 is rolled down may vary. Usually a cuff 20 of about ¼ inch to 1 ½ will be sufficient to reduce by-pass.

Figure 3:
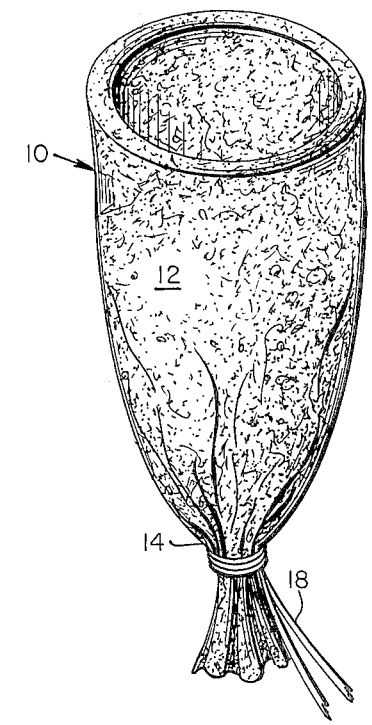
FIG. 3 is a perspective view of the tampon of FIGS. 1 and 2 with the cuff portion having been unfurled on removal.

The tampons 10 of the present invention may be inserted by any of the insertor means which are known to be useful for this purpose. As previously pointed out the tampons are so packed in the insertors that the open end when inserted will face towards the posterior portion of the vagina. In preferred embodiments the insertor will have an annular ring thereon to limit the depth of penetration so that the apex of the tampon will lie just posterior to the hymenal ring. When the tampon has become saturated and swollen the cuff 20 will unfurl as it is removed (see FIG. 3) to ease the removal.

Although not shown it should be understood that the outer wall of the cone may be made of water-impermeable material and the inner wall of permeable material. Further the absorbent material may be made up of a plurality of small pieces of chopped foam (e.g., strands having lengths less than 1 inch and widths from 1/16 to ¼ inch) intermixed with a plurality of small particles of absorbent, hydrophilic, water-insoluble polymers as described above.

Having thus described the invention what is claimed is:

1. A catamenial tampon comprising a hollow cone of absorbent material, said cone being adapted so that the open end of the cone which is the insertable end will face the posterior of the vagina when inserted, a withdrawal cord attached to the outside of the apex at the retrievable closed end of the cone and the walls of the insertable open end of the cone being furled outwardly and down to form a cuff which covers a portion of the outer walls of said cone, said cuff providing a tighter fit with the vaginal walls when the tampon is in position and said cuff unfurling upon removal to ease said removal.

2. A tampon as defined in claim 1 wherein within the walls of the cone there is included a hydrophilic-water-insoluble, highly water absorbent polymer.

3. A tampon as defined in claim 1 wherein the outer circumference of the cuff is between 3 and 6 inches and the tampon is designed to occupy the anterior portion of the vagina just posterior to the hymenal ring.

4. A tampon as defined in claim 1 wherein the cone comprises a water absorbable foam and a mass of water absorbable cellulose fibers encased in a water-permeable non-woven casing.

5. A tampon as defined in claim 1 which is enclosed in an inserter in a manner such that the open end of the cone faces the posterior of the vagina upon insertion.

* * * * *